(12) United States Patent
Van Winkle et al.

(10) Patent No.: US 7,432,416 B2
(45) Date of Patent: Oct. 7, 2008

(54) GENERATION OF PLANTS WITH IMPROVED DROUGHT TOLERANCE

(75) Inventors: Jill Van Winkle, Portland, OR (US); Xing Liang Liu, Tualatin, OR (US); Jonathan R. Fitch, Portland, OR (US); Vladimir Shulaev, Blacksburg, VA (US)

(73) Assignee: Agrigenetics, Inc., Indianapolis, IN (US)

( * ) Notice: Subject to any disclaimer, the term of this patent is extended or adjusted under 35 U.S.C. 154(b) by 0 days.

(21) Appl. No.: 10/509,691

(22) PCT Filed: Mar. 27, 2003

(86) PCT No.: PCT/US03/09479

§ 371 (c)(1), (2), (4) Date: May 8, 2005

(87) PCT Pub. No.: WO03/081988

PCT Pub. Date: Oct. 9, 2003

(65) Prior Publication Data

US 2005/0257294 A1 Nov. 17, 2005

Related U.S. Application Data

(60) Provisional application No. 60/368,650, filed on Mar. 27, 2002.

(51) Int. Cl.
*C12N 15/82* (2006.01)
(52) U.S. Cl. ...................... 800/278; 435/468
(58) Field of Classification Search ........................ None
See application file for complete search history.

(56) References Cited

U.S. PATENT DOCUMENTS

| 5,939,601 | A | 8/1999 | Klessig et al. |
| 5,981,842 | A | 11/1999 | Wu et al. |
| 6,791,012 | B1 | 9/2004 | Chen et al. |
| 2002/0160378 | A1* | 10/2002 | Harper et al. ................. 435/6 |
| 2004/0009476 | A9* | 1/2004 | Harper et al. ................. 435/6 |

FOREIGN PATENT DOCUMENTS

| EP | 1033405 A2 * | 9/2000 |
| WO | WO 0216655 A2 * | 2/2002 |

OTHER PUBLICATIONS

Yanagisawa (Trends in Plant Science, 7:555-560, 2002).*
Alvim et al. (Plant Physiol., 126:1042-1054, Published Jul. 2001).*
Alexandrov et al., Genseq Database, Accession No. AAG27962, EP1033405A2, Sep. 6, 2000.*
Yanagisawa,S. "Dof DNA-Binding Proteins Contain a Novel Zinc Finger Motif.", *Trends Plant Sci.*, Jul. 1996, p. 213-4, 1:7.
Papi, et al., "Identification and disruption of an Arabidopsis Zinc Finger Gene Controlling Seed Germination.", *Genes Dev.*, 2000, p. 28-33, 14.
Zhang, et al., "Interactions Between Distinct Types of DNA Binding Proteins Enhance Binding to ocs Element Promoter Sequences.", *Plant Cell*, Dec. 1995, p. 2241-52, 7.
Eu Arabidopsis Sequencing Project. DNA Binding Protein. GenBank Accession No. CAB88324, p. 1.
Lin et al., "*Arabidopsis thaliana* chromosome 1 BAC F22HF genomic sequence, complete sequence," *Genbank GI*, No. 12331602 (online), Jan. 22, 2001 (retrieved Jan. 14, 2005). Retrieved from the Internet: <URL:http://www.ncbi.nlm.nih.gov/entrez/query.fcgi?CMD=Display&DB=nucleotide>.
Rushton et al., "Synthetic plant promoters containing defined regulatory elements provide novel insights into pathogen-and wound-inducing signaling," *Plant Cell*, 14:749-762, 2002.
Ryan et al., Accession No: T01350. EMBL database, 1999.
Theologis et al. "Sequence and analysis of chromosome 1 of the plant *Arabidopsis thaliana*," *Nature*, 408:816-820, 2000.
Chen et al., "Expression profile matrix of Arabidopsis transcription factor genes suggests their putative functions in response to environmental stresses," *The Plant Cell*, 14(3):559-574, 2002.

* cited by examiner

*Primary Examiner*—Phuong T. Bui
*Assistant Examiner*—Vinod Kumar
(74) *Attorney, Agent, or Firm*—Klarquist Sparkman LLP

(57) ABSTRACT

The present invention is directed to plants that display a drought tolerance phenotype due to altered expression of a DRO2 nucleic acid. The invention is further directed to methods of generating plants with a drought tolerance phenotype.

4 Claims, No Drawings

GENERATION OF PLANTS WITH IMPROVED DROUGHT TOLERANCE

CROSS REFERENCE TO RELATED APPLICATIONS

This is a § 371 U.S. national stage of PCT/US03/09479, filed Mar. 27, 2003, which was published in English under PCT Article 2(2), and claims the benefit of U.S. Provisional Patent Application No. 60/368,650, filed Mar. 27, 2002.

BACKGROUND OF THE INVENTION

Crop production is affected by numerous abiotic environmental factors, with soil salinity and drought having the most detrimental effects. Approximately 70% of the genetic yield potential in major crops is lost due to abiotic stresses, and most major agricultural crops are susceptible to drought stress. Attempts to improve yield under stress conditions by plant breeding have been largely unsuccessful, primarily due to the multigenic origin of the adaptive responses (Barkla et al. 1999, Adv Exp Med Biol 464:77-89).

Considerable effort has focused on the identification of genetic factors that contribute to stress tolerance and on the genetic engineering of crop plants with increased stress tolerance. A number of genes have been identified whose expression or mis-expression is associated with drought tolerance, via a variety of different mechanisms. For instance, transformed tobacco that express maize NADP-malic enzyme display increased water conservation and gained more mass per water consumed than wild-type plants (Laporte et al. 2002, J Exp Bot 53:699-705). Significant research effort has focused on the plant hormone abscisic acid (ABA), which is involved in adaptation to various environmental stresses. Transgenic tobacco and transgenic *Arabidopsis* that overexpress the enzyme 9-cis-epoxycarotenoid dioxygenase (NCED), which is key to ABA biosynthesis, display improved drought tolerance (Qin et al. 2002, Plant Physiol 128:544-51; Iuchi et al. 2001, Plant J 27:325-33). Drought tolerance is often linked to salt tolerance, since both are associated with regulation of osmotic potential and turgor. Accordingly, transgenic plants that overexpress a vacuolar H+pump (H+-pyrophosphatase), which generates a proton gradient across the vacuolar membrane, display improved drought—and salt-stress, due to increased solute accumulation and water retention (Gaxiola et al. 2001, Proc Natl Acad Sci U S A 98:11444-9). Trehalose also contributes to osmoprotection against environmental stress. Potato plants that mis-express trehalose-6-phosphate synthase, a key enzyme for trehalose biosynthesis, show increased drought resistance (Yeo et al. 2000, Mol Cells 10:263-8).

*Arabidopsis* has served as a model system for the identification of genes that contribute to drought tolerance. For instance, researchers have identified numerous genes that are induced in response to water deprivation (e.g., Taji et al. 1999, Plant Cell Physiol 40:119-23; Ascenzi et al., 1997, Plant Mol Biol 34:629-41; Gosti et al. 1995, Mol Gen Genet 246:10-18; Koizumi et al. 1993 Gene 129:175-82) and cis-acting DNA sequences called ABA responsive elements (ABREs) that control ABA or stress responsive gene expression (Giraudat et al. 1994, Plant Mol. Biol. 26: 1557).

Several drought tolerant mutants of *Arabidopsis* have been identified. These include the recessive mutants abh1 (Hugouvieux et al. 2001, Cell 106: 477), era1-2 (Pei et al. 1998, Science 282: 286) and abi1-1Ri (Gosti et al. 1999, Plant Cell 11:1897-1909). The mutants era1-2 and abh1 were identified by screening for seedlings hypersensitive to ABA, while the mutant abi1-1Ri was isolated as an intragenic suppressor of the ABA insensitive mutant abi1-1. Dominant drought tolerant mutants were identified by over-expressing ABF3, ABF4 (Kang et al. 2002, Plant Cell 14:343-357) or DREB1A (Kasuga, 1999 Nature Biotech 17: 287). ABF3 and ABF4 encode basic-region leucine zipper (bZIP) DNA binding proteins that bind specifically ABREs. DREB1A encodes a protein with an EREBP/AP2 DNA binding domain that binds to the dehydration-responsive element (DRE) essential for dehydration responsive gene expression (Liu et al. 1998, Plant Cell 10: 1391). A dominant drought tolerant phenotype in tobacco was obtained by over-expressing the soybean BiP gene (Alvim et al. 2001, Plant Physiol 126, 1042).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi H et al., Science(1992) 258: 1350-1353; Weigel D, et al., Plant Physiology(2000) 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson K et al., Plant Cell(1996) 8: 659-671, Schaffer R, et al., Cell(1998) 93: 1219-1229, Fridborg I et al., Plant Cell 11: 1019-1032, 1999; Kardailsky I et al., Science(1999) 286: 1962-1965; Christensen S et al., 9$^{th}$ International Conference on *Arabidopsis* Research. Univ. of Wisconsin-Madison, Jun. 24-28, 1998. Abstract 165).

We used activation tagging techniques to identify the association between the *Arabidopsis* DNA binding protein OBF1 and drought tolerance. OBF1 was first identified in a screen designed to characterize factors associated with proteins that bind to octopine synthase (ocs) promoter elements (Zhang et al. 1995, Plant Cell 7:2241-2252). The ocs elements are 20 bp DNA motifs that were originally found in the *Agrobacterium* osc promoter and were subsequently identified in the CaMV 35S promoter and in promoters of a class of plant stress-inducible genes such as glutathione S-transferase genes, which may be involved in responses to oxidative stress. Auxins and/or salicylic acid can induce genes with ocs promoter elements, possibly through changes in the redox potential. The *Arabidopsis* OBF4/OBF5 proteins are basic-region leucine zipper (bZIP) transcription factors that have been shown to interact with ocs elements. OBP1 was identified by its ability to bind OBF4 and OBF5, even in the absence of the target ocs elements.

The OPB1 protein sequence predicted by Zhang et al. is presented in Genbank entry GI 1212759 and is 13 amino acids shorter at the N-terminal end than the protein predicted by the *Arabidopsis* sequencing project (i.e., encoded by the same genomic sequence) and presented in GI 7630027.

OBP1 contains a highly conserved Dof domain, a zinc finger DNA-binding domain found in proteins from a number of plant species (Yanagisawa S, 1996, Trends Plant Sci. 1:213-214). OBP1 is constitutively expressed both in aerial portions of the plant and in roots; it is induced by auxin, salicylic acid, and cycloheximide (Kang and Singh, Plant J 21: 329-339, 2000).

SUMMARY OF THE INVENTION

The present invention provides a method of producing an improved drought tolerance phenotype in a plant. The method comprises introducing into plant progenitor cells a vector comprising a nucleotide sequence that encodes or is complementary to a sequence encoding a DRO2 polypeptide and growing a transgenic plant that expresses the nucleotide sequence. In one embodiment, the DRO2 polypeptide has at least 50% sequence identity to the amino acid sequence presented in SEQ ID NO:2 and comprises a DNA binding domain. In other embodiments, the DRO2 polypeptide has at least 80% or 90% sequence identity to or has the amino acid sequence presented in SEQ ID NO:2.

The invention further provides plants and plant parts obtained by the methods described herein.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y.,1989, and Ausubel FM et al. Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality.

An "altered drought tolerance phenotype" refers to detectable change in the ability of a genetically modified plant to withstand low-water conditions compared to the similar, but non-modified plant. In general, improved (increased) drought tolerance phenotypes (i.e., ability to a plant to survive in low-water conditions that would normally be deleterious to a plant) are of interest.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes reference to a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Improved Drought Tolerance Phenotype

We used an *Arabidopsis* activation tagging screen to identify the association between the OBP1 gene (Zhang et al. 1995, supra), which we have designated "DRO2 (for Drought tolerant)," and an improved drought tolerance phenotype. Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al, supra). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 18 seeds were planted, grown for four weeks under adequate water conditions, and then deprived of water for 10-14 days. Plants that did not wilt, and that maintained a high water content were identified as drought tolerant.

An *Arabidopsis* line that showed increased drought tolerance was identified. The association of the DRO2 gene with the drought tolerance phenotype was discovered by analysis of the genomic DNA sequence flanking the T-DNA insertion in the identified line. Accordingly, DRO2 genes and/or polypeptides may be employed in the development of genetically modified plants having a modified drought tolerance phenotype ("a DRO2 phenotype"). DRO2 genes may be used in the generation of crops and/or other plant species that have improved ability to survive in low-water conditions. The DRO2 phenotype may further enhance the overall health of the plant.

DRO2 Nucleic Acids and Polypeptides

*Arabidopsis* DRO2 nucleic acid (cDNA) sequence is provided in SEQ ID NO:1 and in Genbank entry GI 7630025, nucleotides 110251-111012. The corresponding protein sequence is provided in SEQ ID NO:2 and in GI 7630027. A variant polypeptide, encoded by the same genomic sequence, is provided in GI 1212759 (Zhang et al. 1995, supra).

As used herein, the term "DRO2 polypeptide" refers to a full-length DRO2 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active DRO2 polypeptide causes an altered drought tolerance phenotype when mis-expressed in a plant. In a further preferred embodiment, mis-expression of the functionally active DRO2 polypeptide causes improved drought tolerance. In another embodiment, a functionally active DRO2 polypeptide is capable of rescuing defective (including deficient) endogenous DRO2 activity when expressed in a plant or in plant cells; the rescuing polypeptide may be from the same or from a different species as that with defective activity. In another embodiment, a functionally active fragment of a full length DRO2 polypeptide (i.e., a native polypeptide having the sequence of SEQ ID NO:2 or a naturally occurring ortholog thereof) retains one of more of the biological properties associated with the full-length DRO2 polypeptide, such as signaling activity, binding activity, catalytic activity, or cellular or extra-cellular localizing activity. Preferred DRO2 polypeptides display DNA-binding activity. A DRO2 fragment preferably comprises a DRO2 domain, such as a C- or N-terminal or catalytic domain, among others, and preferably comprises at least 10, preferably at least 20, more preferably at least 25, and most preferably at least 50 contiguous amino acids of a DRO2 protein. Functional domains can be identified using the PFAM program (Bateman A et al., Nucleic Acids Res (1999) 27:260-262; website at pfam.wustl.edu). A preferred DRO2 fragment comprises a DNA binding domain, most preferably a Dof-type zinc finger domain (PF02701). Functionally active variants of full-length DRO2 polypeptides or fragments thereof include polypeptides with amino acid insertions, deletions, or substitutions that retain one of more of the biological properties associated with the full-length DRO2 polypeptide. In some cases, variants are generated that change the post-translational processing of a DRO2 polypeptide. For instance, variants may have altered protein transport or protein localization characteristics or altered protein half-life compared to the native polypeptide.

As used herein, the term "DRO2 nucleic acid" encompasses nucleic acids with the sequence provided in or complementary to the sequence provided in SEQ ID NO:1, as well as functionally active fragments, derivatives, or orthologs thereof. A DRO2 nucleic acid of this invention may be DNA, derived from genomic DNA or cDNA, or RNA.

In one embodiment, a functionally active DRO2 nucleic acid encodes or is complementary to a nucleic acid that encodes a functionally active DRO2 polypeptide. Included within this definition is genomic DNA that serves as a template for a primary RNA transcript (i.e., an mRNA precursor) that requires processing, such as splicing, before encoding the functionally active DRO2 polypeptide. A DRO2 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed DRO2 polypeptide, or an intermediate form. A DRO2 polynucleotide can also include heterologous coding sequences, for example, sequences that encode a marker included to facilitate the purification of the fused polypeptide, or a transformation marker.

In another embodiment, a functionally active DRO2 nucleic acid is capable of being used in the generation of loss-of-function DRO2 phenotypes, for instance, via antisense suppression, co-suppression, etc.

In one preferred embodiment, a DRO2 nucleic acid used in the methods of this invention comprises a nucleic acid sequence that encodes or is complementary to a sequence that encodes a DRO2 polypeptide having at least 50%, 60%, 70%, 75%, 80%, 85%, 90%, 95% or more sequence identity to the polypeptide sequence presented in SEQ ID NO:2.

In another embodiment a DRO2 polypeptide of the invention comprises a polypeptide sequence with at least 50% or 60% identity to the DRO2 polypeptide sequence of SEQ ID NO:2, and may have at least 70%, 80%, 85%, 90% or 95% or more sequence identity to the DRO2 polypeptide sequence of SEQ ID NO:2. In another embodiment, a DRO2 polypeptide comprises a polypeptide sequence with at least 50%, 60%, 70%, 80%, 85%, 90% or 95% or more sequence identity to a functionally active fragment of the polypeptide presented in SEQ ID NO:2, such as a DNA binding domain. In yet another embodiment, a DRO2 polypeptide comprises a polypeptide sequence with at least 50%, 60%, 70%, 80%, or 90% identity to the polypeptide sequence of SEQ ID NO:2 over its entire length and comprises a DNA binding domain, most preferably a Dof-type zinc finger domain.

In another aspect, a DRO2 polynucleotide sequence is at least 50% to 60% identical over its entire length to the DRO2 nucleic acid sequence presented as SEQ ID NO:1, or nucleic acid sequences that are complementary to such a DRO2 sequence, and may comprise at least 70%, 80%, 85%, 90% or 95% or more sequence identity to the DRO2 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., supra). In some embodiments, a nucleic acid molecule of the invention is capable of hybridizing to a nucleic acid molecule containing the nucleotide sequence of SEQ ID NO:1 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate). In other embodiments, moderately stringent hybridization conditions are used that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a DRO2 polypeptide can be produced. For example, codons may be selected to increase the rate at which expression of the polypeptide occurs in a particular host species, in accordance with the optimum codon usage dictated by the particular host organism (see, e.g., Nakamura Y et al, Nucleic Acids Res (1999) 27:292). Such sequence variants may be used in the methods of this invention.

The methods of the invention may use orthologs of the Arabidopsis DRO2. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as Arabidopsis, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, Nucleic Acids Res (1994) 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach C and Dveksler G (Eds.) PCR Primer: A Laboratory Manual, Cold Spring Harbor Laboratory Press, N.Y., 1989). For instance, methods for generating a cDNA library from the plant species of interest and probing the library with partially homologous gene probes are described in Sambrook et al. A highly conserved portion of the *Arabidopsis* DRO2 coding sequence may be used as a probe. DRO2 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known DRO2 polypeptides are used for ortholog isolation. Western blot analysis can determine that a DRO2 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., supra. Once the candidate ortholog(s) are identified by any of these means, candidate orthologous sequence are used as bait (the "query") for the reverse BLAST against sequences from *Arabidopsis* or other species in which DRO2 nucleic acid and/or polypeptide sequences have been identified.

DRO2 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., *Methods Enzymol.* (1991) 204:125-39), may be used to introduce desired changes into a cloned nucleic acid.

In general, the methods of the invention involve incorporating the desired form of the DRO2 nucleic acid into a plant expression vector for transformation of in plant cells, and the DRO2 polypeptide is expressed in the host plant.

An isolated DRO2 nucleic acid molecule is other than in the form or setting in which it is found in nature and is identified and separated from least one contaminant nucleic acid molecule with which it is ordinarily associated in the natural source of the DRO2 nucleic acid. However, an isolated DRO2 nucleic acid molecule includes DRO2 nucleic acid molecules contained in cells that ordinarily express DRO2 where, for example, the nucleic acid molecule is in a chromosomal location different from that of natural cells.

Generation of Genetically Modified Plants with a Drought Tolerance Phenotype

DRO2 nucleic acids and polypeptides may be used in the generation of genetically modified plants having a modified, preferably an improved drought tolerance phenotype. Such plants may further display increased tolerance to other abiotic stresses, particular salt-stress and freezing, as responses to these stresses and drought stress are mediated by ABA (Thomashow, 1999 Annu. Revl Plant Physiol. Plant Mol. Biol 50: 571; Cushman and Bohnert, 2000, Curr. Opin. Plant Biol. 3: 117; Kang et al. 2002, Plant Cell 14:343-357; Quesada et al. 2000, Genetics 154: 421; Kasuga et al. 1999, Nature Biotech. 17: 287-291).

The methods described herein are generally applicable to all plants. Drought tolerance is an important trait in almost any agricultural crop; most major agricultural crops, including corn, wheat, soybeans, cotton, alfalfa, sugar beets, onions, tomatoes, and beans, are susceptible to drought stress. Although activation tagging and gene identification are carried out in *Arabidopsis*, the DRO2 gene (or an ortholog, variant or fragment thereof) may be expressed in any type of plant. The invention may directed to fruit- and vegetable-bearing plants, plants used in the cut flower industry, grain-producing plants, oil-producing plants, nut-producing plants, crops including corn (*Zea mays*), soybean (*Glycine max*), cotton (*Gossypium*), tomato (*Lycopersicum esculentum*), alfalfa (*Medicago sativa*), flax (*Linum usitatissimun*), tobacco (*Nicotiana*), and turfgrass (Poaceae family), and other forage crops, among others.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a DRO2 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature.

Expression (including transcription and translation) of DRO2 may be regulated with respect to the level of expression, the tissue type(s) where expression takes place and/or developmental stage of expression. A number of heterologous regulatory sequences (e.g., promoters and enhancers) are available for controlling the expression of a DRO2 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones JD et al, (1992) Transgenic Res 1:285-297), the CsVMV promoter (Verdaguer B et al., Plant Mol Biol (1998) 37:1055-1067) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren MJJ et al., Plant Mol Bio (1993) 21:625-640).

In one preferred embodiment, DRO2 expression is under control of regulatory sequences from genes whose expression is associated with drought stress. For example, when the promoter of the drought stress responsive *Arabidopsis* rd29A gene was used to drive expression of DREB1A, *Arabidopsis* plants were more tolerant to drought, salt and freezing stress and did not have the stunted stature associated with plants over-expressing the DREB1A gene from the CaMV 35S promoter (Kasuga et al, 1999 Nature Biotech 17: 287). Promoters from other *Arabidopsis* genes that are responsive to drought stress, such as COR47 (Welin et al. 1995, Plant Mol. Biol. 29: 391), KIN1(Kurkela and Franck, 1990, Plant Mol. Biol. 15: 137), RD22BP (Abe et al. 1997, Plant Cell 9, 1859), ABA1(Accession Number AAG17703), and ABA3 (Xiong et al. 2001, Plant Cell 13: 2063), could be used. Promoters from drought stress inducible genes in other species could be used also. Examples are the rab17, ZmFer1 and ZmFer2 genes from maize (Bush et al, 1997 Plant J 11:1285; Fobis-Loisy, 1995 Eur J Biochem 231:609), the tdi-65 gene from tomato (Harrak, 2001 Genome 44:368), the His1 gene of tobacco (Wei and O'Connell, 1996 Plant Mol Biol 30:255), the Vupat1 gene from cowpea (Matos, 2001 FEBS Lett 491:188), and CDSP34 from *Solanum tuberosum*(Gillet et al, 1998 Plant J 16:257).

In yet another aspect, in some cases it may be desirable to inhibit the expression of endogenous DRO2 in a host cell. Exemplary methods for practicing this aspect of the invention include, but are not limited to antisense suppression (Smith, et al., *Nature* (1988) 334:724-726; van der Krol et al., Biotechniques (1988) 6:958-976); co-suppression (Napoli, et al, *Plant Cell*(1990) 2:279-289); ribozymes (PCT Publication WO 97/10328); and combinations of sense and antisense (Waterhouse, et al., *Proc. Natl. Acad. Sci. USA* (1998) 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc. Natl. Acad. Sci. USA (1988) 85:8805-8809), a partial cDNA sequence including fragments of 5' coding sequence, (Cannon et al., Plant Molec. Biol. (1990) 15:39-47.), or 3' non-coding sequences (Ch'ng et al., Proc. Natl. Acad. Sci. USA (1989) 86:10006-10010). Cosuppression techniques may use the entire cDNA sequence (Napoli et al., supra; van der Krol et al., The Plant Cell (1990) 2:291-299), or a partial cDNA sequence (Smith et al., Mol. Gen. Genetics (1990) 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, *Arch Virol Suppl*(1999) 15:189-201]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., (1999) *Cur Opin Plant Biol.* 2(2):96-103; Dangond F, Physiol Genomics (2000) 2:53-58; van Hal NL et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a DRO2 Phenotype by Transformation with an Activation Tagging Construct Mutants were generated using the activation tagging "ACT-TAG" vector, pSKI015 (GI 6537289; Weigel D et al., supra). Standard methods were used for the generation of *Arabidopsis* transgenic plants, and were essentially as described in published application PCT WO0183697. Briefly, T0 *Arabi-* dopsis(Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1generation based on herbicide resistance. T2 seed was collected from T1 plants and stored in an indexed collection, and a portion of the T2 seed was accessed for the screen.

Approximately 18 T2 seed from each of line tested were planted in soil. The seed were stratified for 3 days at 4° C. and then grown in the greenhouse for 4 weeks with adequate water. After this time, water was withheld for 10-14 days until most of the plants were severely wilted. T2 lines containing plants that appeared to be non-wilted were identified and their relative water content (RWC) measured. RWC was calculated from the following equation:

RWC=(Fresh Weight-Dry Weight)/(Turgid Weight-Dry Weight)×100.

For RWC analysis, 2-3 leaves were taken from each drought tolerant (non-wilted) individual within a line and pooled. Fresh Weight is the mass of these leaves immediately after the drought treatment. Turgid weight is the mass of these leaves after being rehydrated for 24 h in water. Dry Weight is the mass of these leaves after being air-dried. Control plants had RWC values of approximately 26% while. Plants that had RWC values of at least 50% were identified as drought tolerant.

After identification in the primary screen, putative mutant (i.e., drought-tolerant) lines were re-screened using the protocol described above, with the exception that 18 seeds were planted individually.

The ACTTAG line designated W000017146 was identified as having a dominant drought tolerance phenotype. In the secondary screen, 14 of the 18 plants tested had RWC values of at least 50%.

Example 2

Characterization of the T-DNA Insertion in Plants Exhibiting the Altered Drought Tolerance Phenotype We performed standard molecular analyses, essentially as described in patent application PCT WO0183697, to determine the site of the T-DNA insertion associated with the increased drought tolerance phenotype. Briefly, genomic DNA was extracted from plants exhibiting increased drought tolerance. PCR, using primers specific to the pSKI015 vector, confirmed the presence of the 35S enhancer in plants from line W000017146, and Southern blot analysis verified the genomic integration of the ACTTAG T-DNA and showed the presence of a single T-DNA insertion in the transgenic line.

Inverse PCR was used to recover genomic DNA flanking the T-DNA insertion, which was then subjected to sequence analysis.

The sequence flanking the left T-DNA border was subjected to a basic BLASTN search and/or a search of the *Arabidopsis* Information Resource (TAIR) database (available at the arabidopsis.org website), which revealed sequence identity to F11C1 (GI 7630025), mapped to chromosome 3. Sequence analysis revealed that the T-DNA had inserted in the vicinity (i.e., within about 10 kb) of the gene whose nucleotide sequence is presented as SEQ ID NO:1 and GI 7630025, nucleotides 110251-111012, and which we designated DRO2. This insertion appeared complex; while the upstream end had a normal left border, the downstream end was associated with a fragment of the left border, in addition to the right border, and a small genomic deletion. The right side of the T-DNA insertion (and the right border) was approximately 1.5 kb 5' to the start codon of SEQ ID NO:1.

Example 3

Analysis of *Arabidopsis* DRO2 Sequence

The amino acid sequence predicted from the DRO2 nucleic acid sequence is presented in SEQ ID NO:2 and GI 7630027.

Sequence analyses were performed with BLAST (Altschul et al., 1990, J. Mol. Biol. 215:403-410) and PFAM (Bateman et al., supra), PSORT (Nakai K, and Horton P, 1999, Trends Biochem Sci 24:34-6), among others. PFAM analysis predicted a "Dof (DNA binding with one finger)" zinc finger DNA-binding domain (PF02701; Shimofurutani et al. 1998, FEBS Lett 430:251-256). Dof proteins are a class of transcription factors unique to plants (Yanagisawa, 1996, Biochem Mol Biol Int 38:665-73), containing a highly conserved 52 amino acid motif containing a single Zinc finger ($CX_2CX_{21},CX_2C$). The Dof domain of SEQ ID NO:2 is at amino acids 25-87.

Example 4

Confirmation of Phenotype/Genotype Association

RT-PCR analysis showed that the DRO2 gene was specifically overexpressed in plants from the line displaying the improved drought tolerance phenotype. Specifically, RNA was extracted from tissues derived from plants exhibiting the DRO2 phenotype and from wild type COL-0 plants. RT-PCR was performed using primers specific to the sequence presented as SEQ ID NO:1 and to other predicted genes in the vicinity of the T-DNA insertion. The results showed that plants displaying the DRO2 phenotype over-expressed the mRNA for the DRO2 gene, indicating the enhanced expression of the DRO2 gene is correlated with the DRO2 phenotype.

It is claimed:

1. A method of producing increased drought tolerance in a plant, said method comprising:
   a) introducing into plant cells a plant transformation vector comprising a heterologous constitutive promoter operatively linked to a nucleotide sequence that encodes a DRO2 polypeptide comprising an amino acid sequence having at least 95% sequence identity to the amino acid sequence of SEQ ID NO:2 to produce transformed cells overexpressing the DRO2 polypeptide, wherein overexpression of the DRO 2 polypeptide confers drought tolerance to said plant cells;
   b) growing the transformed cells to produce a transgenic plant and
   c) identifying said transgenic plant with increased drought tolerance by measuring relative water content of the transgenic plant in comparison to an untransformed plant, whereby the drought tolerant transgenic plant has a higher water content than said untransformed plant.

2. The method of claim 1, wherein the nucleotide sequence that encodes the DRO2 polypeptide comprises the amino acid sequence of SEQ ID NO:2.

3. The method of claim 1, further comprising subjecting the plant to water deprivation prior to identifying said transgenic plant with increased drought tolerance.

4. The method of claim 3, wherein subjecting the plant to water deprivation comprises depriving the plant of water for at least 10 days.

* * * * *

SEQUENCE LISTING

<160> NUMBER OF SEQ ID NOS: 2

<210> SEQ ID NO 1
<211> LENGTH: 762
<212> TYPE: DNA
<213> ORGANISM: Arabidopsis thaliana

<400> SEQUENCE: 1

```
atgccgacgt ctgactccgg tgaaccacgg cgaatagcta tgaaacctaa cggcgtaaca    60
gttccgattt ctgaccagca agaacagctt ccatgtcctc gttgtgactc atccaacact   120
aagttctgtt actacaacaa ctacaacttc tctcagcctc gtcacttctg caaagcttgt   180
cgtcgttact ggactcacgg tggtactctc cgtgacgttc ctgtcggtgg tggtactcgt   240
aaaagcgcga aacgttcccg cacttgctcg aactcttctt cctcctctgt ttctggtgtc   300
gtctctaact ctaacggtgt tccgttacaa acgacgcctg ttctcttccc tcagtcgtca   360
atctctaacg gcgttactca cacagtaact gaaagcgacg gaaagggaag tgctttatct   420
ctctgtggaa gtttcacctc cactctgttg aaccataacg ctgctgcgac ggctacgcat   480
ggatccggtt cggttattgg tatcggaggt tttggaatcg gactcgggtc gggttttgat   540
gacgtcagct ttggactcgg aagagcgatg tggccgtttt caactgttgg tactgcgaca   600
acgacgaatg ttgggagtaa cggtggtcat cacgctgttc caatgccagc cacgtggcag   660
ttcgagggt tagagagcaa cgctggtggt ggatttgtct ccggtgagta ctttgcgtgg   720
ccggatcttt ccatcacaac tccgggaaac tcactcaaat ga                     762
```

<210> SEQ ID NO 2
<211> LENGTH: 253
<212> TYPE: PRT
<213> ORGANISM: Arabidopsis thaliana

<400> SEQUENCE: 2

```
Met Pro Thr Ser Asp Ser Gly Glu Pro Arg Arg Ile Ala Met Lys Pro
1               5                   10                  15

Asn Gly Val Thr Val Pro Ile Ser Asp Gln Gln Glu Gln Leu Pro Cys
            20                  25                  30

Pro Arg Cys Asp Ser Ser Asn Thr Lys Phe Cys Tyr Tyr Asn Asn Tyr
        35                  40                  45

Asn Phe Ser Gln Pro Arg His Phe Cys Lys Ala Cys Arg Arg Tyr Trp
    50                  55                  60

Thr His Gly Gly Thr Leu Arg Asp Val Pro Val Gly Gly Thr Arg
65                  70                  75                  80

Lys Ser Ala Lys Arg Ser Arg Thr Cys Ser Asn Ser Ser Ser Ser
                85                  90                  95

Val Ser Gly Val Val Ser Asn Ser Asn Gly Val Pro Leu Gln Thr Thr
            100                 105                 110

Pro Val Leu Phe Pro Gln Ser Ser Ile Ser Asn Gly Val Thr His Thr
        115                 120                 125

Val Thr Glu Ser Asp Gly Lys Gly Ser Ala Leu Ser Leu Cys Gly Ser
    130                 135                 140

Phe Thr Ser Thr Leu Leu Asn His Asn Ala Ala Ala Thr Ala Thr His
145                 150                 155                 160

Gly Ser Gly Ser Val Ile Gly Ile Gly Gly Phe Gly Ile Gly Leu Gly
                165                 170                 175

Ser Gly Phe Asp Asp Val Ser Phe Gly Leu Gly Arg Ala Met Trp Pro
            180                 185                 190

Phe Ser Thr Val Gly Thr Ala Thr Thr Thr Asn Val Gly Ser Asn Gly
        195                 200                 205

Gly His His Ala Val Pro Met Pro Ala Thr Trp Gln Phe Glu Gly Leu
    210                 215                 220

Glu Ser Asn Ala Gly Gly Gly Phe Val Ser Gly Glu Tyr Phe Ala Trp
225                 230                 235                 240
```

-continued

```
Pro Asp Leu Ser Ile Thr Thr Pro Gly Asn Ser Leu Lys
                245                 250
```